US006458888B1

(12) United States Patent
Hood et al.

(10) Patent No.: US 6,458,888 B1
(45) Date of Patent: Oct. 1, 2002

(54) RHEOLOGY MODIFIER FOR USE IN AQUEOUS COMPOSITIONS

(75) Inventors: David K. Hood, Basking Ridge; Stephen L. Kopolow, Plainsboro; Michael Tallon, Aberdeen; Yoon Tae Kwak, Woodcliff Lake; Laurence Senak, West Orange; Drupesh Patel; John Mc Kittrick, both of Jersey City, all of NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/882,418

(22) Filed: Jun. 15, 2001

Related U.S. Application Data

(63) Continuation-in-part of application No. 09/663,010, filed on Sep. 15, 2000, and a continuation-in-part of application No. 09/784,268, filed on Feb. 15, 2001.

(51) Int. Cl.$^7$ .................................................. C08L 39/00
(52) U.S. Cl. ......................................................... 524/808
(58) Field of Search .......................................... 524/808

(56) References Cited

U.S. PATENT DOCUMENTS 5,997,855 A * 12/1999 Liu .......................... 424/78.24

* cited by examiner

Primary Examiner—Edward J. Cain
(74) Attorney, Agent, or Firm—Walter Katz; William J. Davis; Marilyn J. Maue

(57) ABSTRACT

A rheology modifier for use in aqueous or alcoholic compositions includes an aqueous two-phase polymeric composition of by weight, 5–75% of (a) a water-soluble polymer having (b) in situ-formed, substantially water-insoluble resinous particles of said polymer substantially uniformly dispersed therein, and (c) 25–95% of water.

22 Claims, 2 Drawing Sheets

COMPARISON OF BROOKFIELD VISCOSITY versus Φ

RHEOLOGY MODIFIER FOR USE IN AQUEOUS COMPOSITIONS

CROSS-REFERENCE TO RELATED U.S. PATENT APPLICATIONS

This application is a continuation-in-part of co-pending U.S. patent applications Ser. No. 09/663,010, filed Sep. 15, 2000, and Ser. No. 09/784,268, filed Feb. 15, 2001.

BACKGROUND OF THE INVENTION

1. Field of the Invention

This invention relates to rheology modifiers used to adjust the rheological properties of polymeric compositions, and, more particularly, to non-continuous, vinyl lactam polymeric compositions with two-phases therein, having advantageous rheology properties in commercial applications.

2. Description of the Prior Art

Rheology modifiers are used generally to adjust or modify the rheological properties of aqueous compositions. Such properties include, without limitation, viscosity, flow rate, stability to viscosity change over time, and the ability to suspend particles in such aqueous compositions. The particular type of modifier used usually depends on the particular aqueous composition to be modified and on the end-use of the modified aqueous composition. Examples of conventional rheology modifiers include thickeners such as cellulosic derivatives, polyvinyl alcohol, sodium polyacrylate, and other water-soluble macromolecules, and copolymeric emulsions in which monomers with acid groups have been introduced onto the main chain. Such thickeners are used widely in fiber treatment and adhesives.

The rheological properties of concentrated dispersions are critical to many important commercial applications. Examples include coatings, inks, films, oils, paints, food additives and pharmaceuticals. Accordingly, the microscopic and macroscopic dispersion structure and the resulting flow properties of such systems are of both scientific and practical interest. The art has established that sub-micron particles in such systems can have a dramatic effect on the rheology of a polymeric solution or fluid. Several physical critical parameters have been identified as influencing its rheology, including the dispersed particle volume fraction, particle size shape and distribution, the continuous phase viscosity and the fluid flow field. By altering or adjusting these microscopic parameters, certain macroscopic phenomena such as elasticity, shear thinning, thixotropic effect and shear thickening can be modified for a particular application or to exhibit a desired property.

Polymeric compositions of vinyl lactam monomers generally are one-phase, soluble, high viscosity materials. These compositions are useful in a variety of commercial applications such as film formers, dye transfer inhibitors, dispersants, excipients and drug delivery. Aqueous gels of these monomers can also be prepared by light covalent or associative crosslinking of polymer chains resulting in one-phase materials of high viscosity which are effective thickeners in personal care formulations, particularly hair care products.

The prior art in this field is represented by the following patents.

Niessner, in U.S. Pat. Nos. 5,149,750 and 5,180,804, disclosed finely divided, water-swellable gel-like, water-swellable copolymers by polymerization of comonomers in the presence of a surfactant.

Liu, in U.S. Pat. No. 5,997,855, described a homogeneous terpolymer for hair care use, however, without a crosslinking agent.

Kopolow, in U.S. Pat. No. 5,130,121, described personal care compositions containing a stabilized cosmetically-active product obtained by in situ polymerization of a water-soluble vinyl monomer in the presence of discrete microdroplets of a cosmetically-active oil in water.

Blankenburg, in U.S. Pat. Nos. 5,635,169 and 6,107,397, described uncrosslinked aqueous copolymer dispersions of nonionic water-soluble monomers with N-vinyl groups and hydrophobic monomers.

Steckler, in U.S. Pat. No. 3,878,175, disclosed highly absorbent spongy gel polymer materials by simultaneous copolymerization and partial crosslinking of a comonomer mixture of an alkyl acrylate and a heterocyclic N-vinyl monomer containing a carbonyl functionality in the presence of a hydrophobic liquid diluent in which the final polymer is insoluble.

Markus, in U.S. Pat. No. 2,810,716, described a process for making swellable resins by copolymerizing monomers in the presence of a water-soluble non-redox divalent-ion containing salt.

Tseng, in U.S. Pat. Nos. 5,393,854 and 5,717,045, disclosed a one-phase, aqueous gel of crosslinked copolymers of vinyl pyrrolidone and dimethylaminoethyl methacrylate for use in hair care products. The crosslinking agent was 1-vinyl-3-(E)-ethylidene pyrrolidone. The gels had a Brookfield viscosity of between 60,000 and 100,000.

These references illustrate the desire of the art to produce a continuous network of polymer molecules, or microgel, which is a one-phase system, and of high viscosity.

Accordingly, it is an object of this invention to provide a new and improved rheology modifier composition to adjust the rheological properties of commercial products.

A particular object of the present invention is to provide a rheology modifier which is an aqueous polymeric composition of a water-soluble polymer, and including in situ-formed, minute resinous particles dispersed therein, that, under suitable light magnification, shows the presence of two-discrete phases therein, one being the water soluble polymer and the other being water-insoluble resinous particles.

IN THE DRAWINGS

SUMMARY OF THE INVENTION

Figure 1:
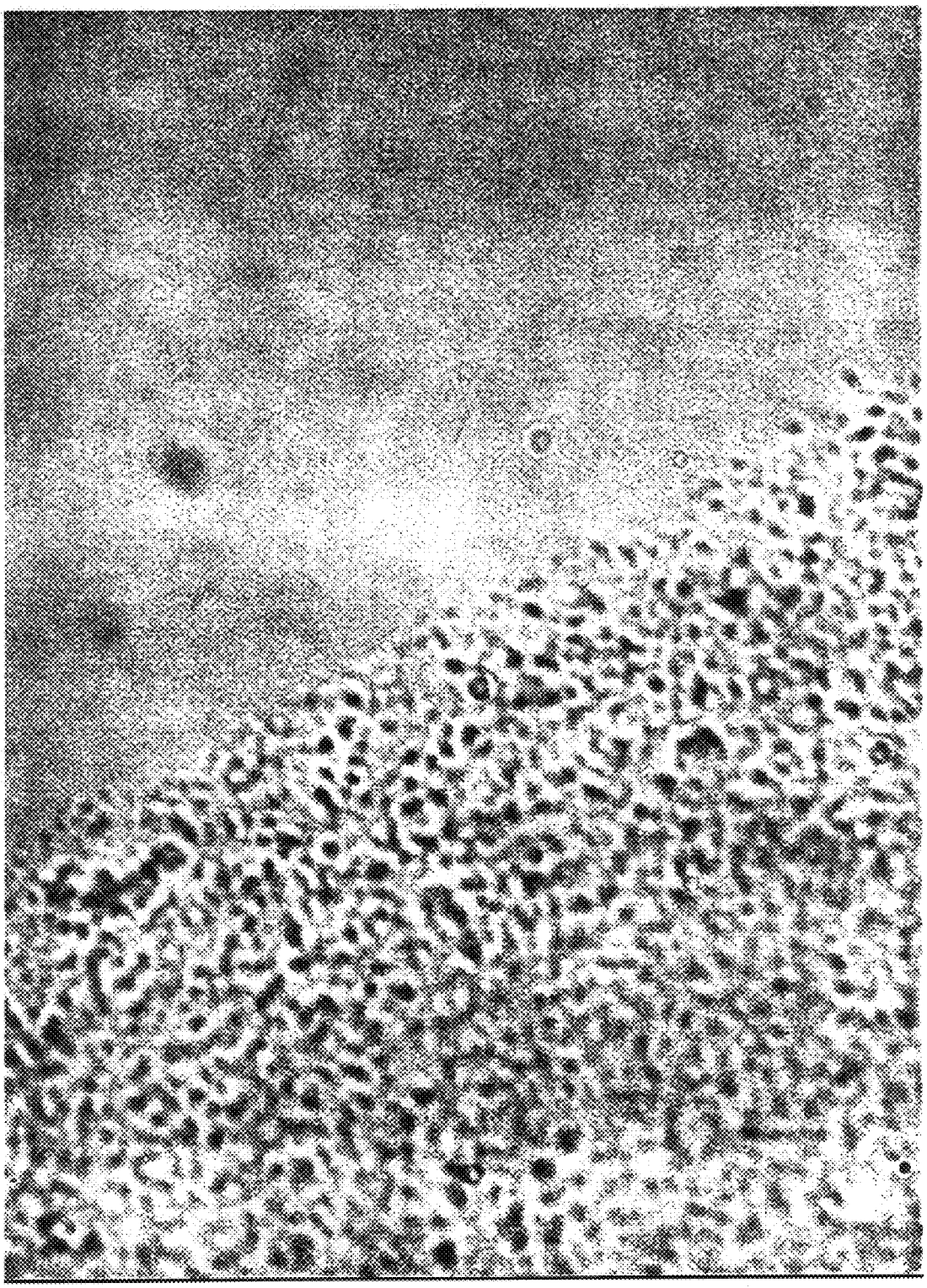
FIG. 1 is a photomicrograph of the aqueous polymeric composition of the invention showing the presence of two discrete phases therein.

What is described herein is a rheology modifier for use in aqueous or alcoholic compositions which includes a stable, aqueous polymeric composition which forms a clear to translucent film upon application to a substrate comprising, by weight, 5–75% of (a) a water-soluble polymer having (b) in situ-formed, substantially water-insoluble resinous particles of said polymer substantially uniformly dispersed therein, and (c) 25–95% of water.

Preferably, the polymer is polyvinylpyrrolidone (PVP), poly(vinylcaprolactam) (PVCL), a copolymer of PVP and/or PVCL, and, optionally, one or more comonomers, including comonomers such as dimethylaminopropyl(meth)acrylamide (DMAPMA) and dimethylaminoethyl(meth)acrylate (DMAEMA). Preferably, the polymer is a vinyl lactam polymer, optionally copolymerized with a methacrylate/acrylate and/or methacrylamide/acrylamide comonomer.

In this invention, the composition includes particles having a size of <500μ, preferably <100μ, and optimally between >1 nm and <500μ.

Suitably, the composition includes a substantially water-insoluble polymer which is a crosslinked or branched polymer, neutralized and/or quaternized, and/or functionalized quaternized. The ratio of (a):(b) is 20–95% to 5–80%, preferably 20–75% to 25–80%, and the crosslinking agent is a substantially water-insoluble compound, preferably pentaerythritol triallyl ether (PETE), or pentaerythritol tetraacrylate (PETA), preferably at least partially soluble in water, and the crosslinking agent is present in an amount of 0.02–0.5% by weight of said composition, most preferably 0.05–0.3%.

In this invention, the composition, prior to modification, has a Brookfield viscosity of 1,000 to 45,000 cps, preferably 2,000 to 20,000.

As a feature of the invention, there is provided herein a process for making a stable, aqueous polymeric composition which includes the steps of providing a reaction mixture of a water-soluble vinyl monomer, optionally with one or more water-soluble comonomers, a predetermined amount of a crosslinking agent and water, heating the mixture, then periodically adding a predetermined amount of an initiator, and polymerizing at about 30–130° C., optionally further including the step of diluting with water during or after the polymerization.

Suitably, the crosslinking agent is present in an amount of 0.02–0.5 wt. % based on monomers present, and preferably is PETE or PETA, and the initiator is an azo initiator.

Another feature of the invention is the provision of formulations containing the above-described composition, made by such process, and films of the composition on a substrate.

The compositions herein may be dried if desired to provide the polymeric composition as a solid, and, if desired, the water soluble polymer extracted with a solvent. The dried stable polymeric composition thereby includes, by weight, (a) 20% to 95% of a water-soluble polymer, and (b) 5% to 80% of in situ-formed, substantially water-insoluble resinous particles of said polymer substantially uniformly dispersed therein.

DETAILED DESCRIPTION OF THE INVENTION

In accordance with this invention, there is provided herein an aqueous or alcoholic polymeric composition having two phases therein, a water-soluble polymeric phase and a discrete, water-insoluble polymer particle phase which is generated in-situ during the polymerization of the monomers. In the preferred forms of the invention, the polymerization is carried out in aqueous solution of a vinyl lactam monomer, such as vinyl pyrrolidone or vinyl caprolactam. Optionally a comonomer may be present to form a copolymer. Suitable comonomers include methacrylate/acrylate monomers, such as dimethylaminoethyl(meth)acrylate (DMAEMA) and/or methacrylamide/acrylamide monomers, such as dimethylaminopropylacrylamide (DMAPMA).

This stable, aqueous polymeric composition forms a clear to translucent film upon application to a substrate and comprises, by weight, 5–75% of (a) a water-soluble polymer having (b) in situ-formed, substantially water-insoluble resinous particles of said polymer substantially uniformly dispersed therein, and (c) 25–95% of water.

The invention will now be illustrated in more detail by reference to the following examples.

EXAMPLE 1

Two-Phase Polymeric Composition of VP/DMAPMA

1. To a 2-l kettle fitted with a nitrogen inlet tube, thermocouple, agitator, and feed lines was added 87.15 g of vinyl pyrrolidone monomer, (VP), 697 g DI water and 0.275 g (0.25% based upon monomer) of pentaerythritol triallyl ether (PETE) as crosslinker.
2. Purged with nitrogen subsurface for 30 minutes.
3. Heated to 70° C.
4. In a separate container weighed out 22.69 g of dimethylaminopropyl methacrylamide (DMAPMA).
5. With kettle temperature at 70° C., stop subsurface nitrogen purge and purged above surface. Precharged 1.1 g DMAPMA from container.
6. Started continuous addition of the remaining DMAPMA (21.86 g) over 210 minutes at a flow rate 0.11 ml/minute. Once the DMAPMA flow started, initiated with first shot of Vazo® 67 in isopropanol (IPA) (Time 0).
7. Initiator was added in 5 separate shots at 0, 30, 60, 150 and 210 minutes. 0.2 g of Vazo® 67 in 1.0 g IPA was added for each shot and two 0.5 g IPA washes were made.
8. Held the reaction temperature overnight at 70° C.
9. When residual VP level was below 400 ppm, diluted the batch with 266.7 g of DI water.
10. Cooled batch to 50° C.
11. Neutralized the batch with conc. HCl to pH of 6.2–6.8 at 50° C. Room temperature pH was 6.8–7.2. Required approximately 14 g of conc. HCl.
12. Added 0.15 to 0.19% BTC 50 NF as preservative.
13. A two-phase, aqueous polymeric composition as shown in the Figure was obtained.

EXAMPLE 2

The process of Example 1 was repeated using 5 separate shots of 0.3 g each of Vazo® 67 in 1.0 g of IPA. A similar polymeric composition as in Example 1.

EXAMPLE 3

The process of Example 1 was repeated using 5 separate shots of 0.4 g each of Vazo® 67 in 1 g of IPA, and 0.3 g of crosslinker. A similar polymeric composition was obtained.

Results

The results of these tests, shown in Table 1 below establish that the 2-phase polymeric composition of the invention exhibits advantageous viscosity properties.

TABLE 1

| Ex. No. | Crosslinker (%) | Initiator (g/shot) | Viscosity (cps) |
|---|---|---|---|
| 1 | 0.25 | 0.2 | 28,200 |
| 2 | 0.25 | 0.3 | 13,000 |
| 3 | 0.3 | 0.4 | 12,800 |

EXAMPLE 4

Polymeric Composition of PVP

1. To a 2-l kettle fitted with a nitrogen inlet tube, thermocouple, agitator, and feed lines was added 131.81 g of VP, 756 g DI water and 0.197 g PETE (0.15% based upon monomer).
2. Purged with nitrogen subsurface for 30 minutes.

3. Heated to 70° C.
4. Initiator was added at 0 and 30 minutes. 0.48 g of Vazo® 67 in 1.5 g IPA was added for each shot and two 1.0 g IPA washes were made.
5. Held the reaction temperature overnight at 70° C.
6. When residual VP was below 400 ppm, diluted the batch with 320.04 g DI water.
7. Cooled batch to 50° C.
8. Added 0.15 to 0.19% BTC 50 NF as preservative.
9. The product was a 2-phase, polymerization composition with 40 to 70% resinous particles, whose soluble fraction had a weight average molecular weight of 1,200,000 to 1,500,000.

EXAMPLE 5

Polymeric Composition of VP/DMAPMA/ Quaternized with Diethyl Sulfate

1. To a 2-l, kettle fitted with a nitrogen inlet tube, thermocouple, agitator, and feed lines was added 96.00 g of VP, 702.7 g DI water and 0.36 g PETE (0.30% based upon monomer).
2. Purged with nitrogen subsurface for 30 minutes.
3. Heated to 70° C.
4. In a separate container weighed out 24.0 g DMAPMA and 74.7 g DI water. Purged with nitrogen.
5. When kettle temperature was at 70° C., stopped subsurface nitrogen purge and purged above surface. Precharged 4.94 g DMAPMA/water from container.
6. Started continuous addition of the remaining DMAPMA/ water (93.76 g) over 210 minutes. Flow rate 0.48 ml/minute. Once DMAPMA/water flow started, initiated with first shot of Vazo® 67 in IPA (Time 0).
7. Initiator was added at 0, 30, 60, 150 and 210 minutes. 0.44 g of Vazo 67 in 1.3 g IPA was added for each shot and two 0.7 g IPA washes were made.
8. Held the reaction temperature overnight at 70° C.
9. When residual VP was below 400 ppm, diluted the batch with 297.5 g DI water.
10. Cooled batch to 50° C.
11. Neutralized the batch with 19.56 g diethyl sulfate (DES) over 60 minutes; at flow rate of 0.28 g/ml.
12. Stirred for 2 hours.
13. Product.

EXAMPLE 6

VP/DMAPMA/PETE Neutralized with Benzophenone-4

1. To a 2-l kettle fitted with a nitrogen inlet tube, thermocouple, agitator, and feed lines was added 87.15 g of HPVP, 630 g DI water and 0.33 g PETE (0.30% based upon monomer).
2. Purged with nitrogen subsurface for 30 minutes.
3. Heated to 70° C.
4. Weighed out 22.69 g DMAPMA and 67 g DI water. Purged with nitrogen.
5. When kettle temperature was at 70° C., stopped subsurface nitrogen purge and purged above surface. Precharged 4.23 g DMAPMA/water from container.
6. Started a continuous addition of the remaining DMAPMA/water (85.46 g) over 210 minutes. Flow rate 0.40 ml/minute. Once DMAPMA/water flow started, initiated with first shot of Vazo® 67 in IPA (Time 0).
7. Initiator was added at 0, 30, 60, 150 and 210 minutes. 0.4 g of Vazo® 67 in 1.0 g IPA was added for each shot and two 0.5 g IPA washes were made.
8. Held the reaction temperature overnight at 70° C.
9. When residual VP was below 400 ppm, diluted the batch with 266.7 g DI water.
10. Cooled batch to 50° C.
11. Neutralized the batch with benzophenone-4, 5 to 99 mole % (2 to 38.6 g respectively). Continued neutralization with sulfuric acid to pH of 6.8 to 7.8 at 50° C.
12. Cooled and discharged.
13. Product.

EXAMPLE 7

VP/DMAPMA/PETA

1. To a 2-l kettle fitted with a nitrogen inlet tube, thermocouple, agitator, and feed lines was added 104.58 g of HPVP, 756 g DI water and 0.59 g pentaerythritol tetraacrylate (0.30% based upon monomer).
2. Purged with nitrogen subsurface for 30 minutes.
3. Heated to 70° C.
4. In a separate container, weighed out 27.23 g DMAPMA and 80.4 g DI water. Purged with nitrogen.
5. When kettle temperature was at 70° C., stopped subsurface nitrogen purge and purged above surface. Precharged 5.38 g DMAPMA/water from container.
6. Started continuous addition of the remaining DMAPMA/ water (102.25 g) over 210 minutes. Flow rate 0.52 ml/minute. Once DMAPMA/water flow started, initiated with first shot of Vazo®67 in IPA (Time 0).
7. Initiator was added at 0, 30, 60, 150 and 210 minutes. 0.16 g of Vazo® 67 in 1.0 g IPA was added for each shot and two 0.5 g IPA washes were made.
8. Held the reaction temperature overnight at 70° C.
9. When VP was below 400 ppm, diluted the batch with 266.7 g DI water.
10. Cooled batch to 50° C.
11. Neutralized the batch with conc. sulfuric acid to pH of 6.6 to 7.8 at 25° C.
12. Added 0.15 to 0.19% BTC 50 NF as preservative.
13. Product.

EXAMPLE 8

Crosslinked Vinyl Caprolactam/DMAPMA Copolymer

1. To a 2-l kettle fitted with a nitrogen inlet tube, thermocouple, agitator and feed lines was added 130.7 g vinyl caprolactam, 128.7 g DI water, 17.1.6 g ethanol, and 0.88 g PETE (0.6% based upon monomer).
2. Purged with nitrogen for 30 minutes.
3. Heated to 70° C.
4. In a syringe pump was added 32.98 g DMAPMA and 171.6 g DI water.
5. At 70° C. added 40 ml of the DMAPMA/water mixture to the kettle and added the first shot of initiator, 0.075 g Vazo® 67 in 0.75 g ethanol. Washed with 0.75 g ethanol.
6. Started addition of the remaining DMAPMA/water mixture (Time 0) from the syringe pump at a rate of 0.34 ml/min, added over 480 minutes.
7. At time 60, 120, 180, 240, 300, 360, 420 and 480 minutes added a shot of Vazo® 67, 0.075 g in 0.75 g ethanol. Washed with 0.75 g ethanol.
8. Held at 70° C. overnight.
9. Cooled reaction to 30° C. and added 415.6 g DI water.
10. Mixed until uniform and then added 544.4 g DI water and 15.38 g hydrochloric acid.
11. Mixed for 2 hours. Adjusted pH to 6.6 to 7.8 with hydrochloric acid, if necessary.

12. Added 0.15 to 0.19% BTC-50 NF as preservative.
13. Product.

EXAMPLE 9

VP/DMAEMA/PETE Process

1. To a 2-l kettle fitted with a nitrogen inlet tube, thermocouple, agitator, and feed lines is added 87.15 g of HPVP, 630 g DI water and 0.33 g (0.30% based upon monomer) pentaerythritol triallyl ether.
2. Purged with nitrogen subsurface for 30 minutes.
3. Heated to 70° C.
4. In a separate container, weighed out 22.69 g DMAEMA and 67 g DI water. Purged with nitrogen.
5. When kettle temperature was at 70° C., stopped subsurface nitrogen purge and purged above surface. Precharged 4.23 g DMAEMA/water from container.
6. Started continuous addition of the remaining DMAEMA/water (85.46 g) over 210 minutes. Flow rate 0.40 ml/minute. Once DMAEMA/water flow started initiator addition with first shot of Vazo 67 in IPA (Time 0).
7. Initiator was added at 0, 30, 60, 150, and 210 minutes. 0.4 g of Vazo 67 in 1.0 g IPA was added for each shot and two 0.5 g IPA washes were made.
8. Held the reaction temperature overnight at 70° C.
9. When VP was below 400 ppm, diluted the batch with 266.7 g DI water.
10. Cooled batch to 50° C.
11. Neutralized the batch with conc. HCl to pH of 6.2 to 6.8 at 50° C. Room temperature pH will be 6.8 to 7.2. Required approximately 14 g of conc. HCl.
12. Added 0.15 to 0.19% BTC 50 NF as preservative.

EXAMPLE 10

Drying of Example 9

The solution of Example 9 was dried on a drum dryer to a solids of >95%. The Tg of the powder was 167° C. Then it was reconstituted in water and found to provide the same waterproofing as the original solution.

EXAMPLE 11

Particle Isolation and Properties 95.2 g of approximately 10% solids polyvinylpyrrolidone/PETE was diluted in 2-liters of distilled water and stirred until thoroughly mixed. A second solution was prepared by taking 500 ml of the first solution and diluting in 2-liters of distilled water. Stirred until thoroughly mixed. Poured the second solution into four 16 oz. jars and centrifuged at ~2250 rpm for about 90 minutes. A white precipitate was observed on the bottom of each 16 oz. jar. The precipitate was removed, via pipette, and placed into four 8-dram vials, respectively. The four 8-dram vials were centrifuged at ~3000 rpm for 60 minutes. The particle size on the precipitate was measured using a Microtrak UPA and found to be about 4 nm.

EXAMPLE 11A

The precipitate obtained in Example 11 in three 8-dram vials was dried, in vacuo, in a 40° C. oven overnight. The result was a thin, generally clear film upon visual observation. This material was then exposed to either methanol, diethyl ether and n-heptane. After 24 hours, methanol had re-dispersed the material. Diethyl ether and n-heptane did not appear to effect the dried material. After 14 days, all samples exhibited a similar appearance to the original 24 hour observations. The particle size on the methanol dispersed material was measured using a Microtrak UPA and found to be about 4 microns.

COMPARATIVE EXAMPLE 12

An aqueous solution of 119.64 g of vinyl pyrrolidone monomer, 0.36 g pentaerythritol trially ether (PETE), 0.6 g of Vazo 67, and 480 g water was charged to a kettle and purged with nitrogen. The reaction mixture was then heated to 65° C. while stirring at 650 rpm. Within 25 minutes the product became so viscous that the reaction was stopped. The product was a continuous gel only.

COMPARATIVE EXAMPLE 13

An aqueous solution of 119.64 g of vinyl pyrrolidone monomer, 0.36 g pentaerythritol triallyl ether (PETE), 0.23 g of Vazo 67, and 480 g water was charged to a kettle and purged with nitrogen. The reaction mixture was then heated to 65° C. while stirring at 650 rpm. After 2 hours at 65° C., the reaction was heated to 95° C. for 1 hour. The product was a viscous solution only.

EXAMPLE 14

| DPI Film Coating Formulation | |
|---|---|
| Ingredient | Parts by Weight |
| VP/DMAPMA/PETE (Ex. 1) | 2.00 |
| PV-OH (88% hydrolyzed) | 8.00 |
| Sequrez ® 755 (glyoxyl) | 0.75 |
| Water | 89.25 |
| | 100.00 |

EXAMPLE 15

| UV Coating Formulation | |
|---|---|
| Ingredient | Parts by Weight |
| VP/DMAPMA/PETE/BENZO-4 (Ex. 6) | 2.00 |
| PV-OH (88% hydrolyzed) | 8.00 |
| Sequrez ® 755 (glyoxyl) | 0.75 |
| Water | 89.25 |
| | 100.00 |

EXAMPLE 16

| Sunscreen Cream | |
|---|---|
| Ingredients | Wt. % |
| PHASE A | |
| Deionized water | 15.69 |
| Disodium EDTA | 0.10 |
| Acrylates/Steareth-20 Methacrylate Copolymer | 1.00 |
| Acrylates Copolymer | 1.00 |
| Hexylene Glycol | 1.00 |

-continued

Sunscreen Cream

| Ingredients | Wt. % |
|---|---|
| Glyceryl Polymethacrylate and Propylene Glycol and PVM/MA Copolymer | 0.50 |
| VP/DMAPMA/PETE/Benzophenone-4 Copolymer (Ex. 6) | 50.00 |
| PHASE B | |
| Glyceryl Stearate and Behenyl Alcohol and Palmitic and Stearic Acid and Lecithin and Lauryl and Myristyl Alcohol and Cetyl Alcohol | 5.00 |
| Oxybenzone | 3.00 |
| Octyl Salicylate | 3.00 |
| Tridecyl Neopentanoate | 2.00 |
| Octyl Palmitate | 6.00 |
| Myristyl Myristate | 1.00 |
| PHASE C | |
| Deionized Water | 5.00 |
| NaOH, 10% Solution | 1.26 |
| PHASE D | |
| Diazolidinyl Urea and Iodopropynyl Butylcarbamate | 0.50 |
| Methyl Paraben | 0.20 |
| Hexylene Glycol | 1.00 |
| PHASE E | |
| Fragrance | 0.25 |

Procedure
1. Combine ingredients in Phase A and heat to 70–75° C.
2. Combine ingredients in Phase B and mix and heat to 70–75° C.
3. Add Phase B to Phase A under homogenization.
4. Add Phase C to the batch under homogenization and homogenize for 15 minutes.
5. Switch to propeller mixing and cool to 45° C.
6. Add Phase D at 45° C. Add Phase E at 40° C. QS with water.

The UV absorbance of the cream was enhanced by the presence of the polymeric composition of the invention therein, as compared to similar formulations without this composition, generally an increase of about 2–3 SPF numbers.

EXAMPLE 17

Clear Styling/Conditioning Gel

| Ingredients | Wt. % |
|---|---|
| Deionized Water | 74.60 |
| Ethanol (190 Proof) | 5.00 |
| VP/DMAPMA/PETE Copolymer (Ex. 1) | 20.00 |
| Dimethicone Copolyol | 0.10 |
| Caprylyl Pyrrolidone | 0.10 |
| Panthenol | 0.10 |
| 2,4-Dihydroxy-N-(3-hydroxypropyl)-3,3-Dimethyl Butanamide | |
| Diazolidinyl Urea and Iodopropynyl Butylcarbamate | 0.10 |
| Perfume | qs |

Manufacturing Procedure
1. In a vessel, add ethanol to water and stir until homogeneous.
2. Next, add VP/DMAPMA/PETE copolymer to the mixture and stir well until homogeneous.
3. Add dimethicone copolyol, panthenol and caprylyl pyrrolidone to the mixture and stir well after each addition until homogeneous.
4. Next, add diazolidinyl urea and iodopropynyl and butylcarbamate and stir well until homogeneous.

EXAMPLE 18

Rinse-Off Protection Hair Conditioner

| Ingredients | Wt. % |
|---|---|
| Deionized Water | 81.73 |
| Emulsifying Wax NF | 4.00 |
| Cetearyl Alcohol and Ceteareth-20 | 2.00 |
| Propylene Glycol | 1.00 |
| VP/DMAPMA/PETE Neutralized with Benzophenone-4 (Ex. 6) | 10.00 |
| Glycerin 99.7% | 0.50 |
| Lauryl Pyrrolidone | 0.25 |
| Citric Acid FCC, USP, Anhydrous | 0.02 |
| Propylene Glycol and Diazolidinyl Urea and Iodopropynyl butylcarbamate | 0.50 |

Manufacturing Procedure
1. Heat the water, propylene glycol, glycerin, and citric acid to 80–85° C. using continuous addition with a propeller stir rod.
2. Add the VP/DMAPMA/PETE neutralized with Benzophenone-4 and stir to homogeneous.
3. Combine in a separate vessel lauryl pyrrolidone, emulsifying wax NF, cetearyl alcohol and ceteareth-20, heating to 80–85° C. mixing until homogeneous.
4. Add, product step 3, to the water phase with good agitation. Mix with continuous agitation for 10–20 minutes or longer. Maintain temperature at 80–85° C. during this step.
5. Begin cooling with continuous agitation until approximately 45° C. Do not force cool.
6. Switch to a paddle mixing rod. Continue slow agitation and cool until a temperature of 30–35° C. is reached. At 30–35° C. add the propylene glycol and diazolidinyl urea and iodopropynyl butylcarbamate and continue mixing until 25° C. is reached.

EXAMPLE 19

Rheology Modifiers

A 5% aqueous polymer solution of VP/DMAPMA/PETE/sulfuric acid (Ex. 1) was thoroughly mixed with a 5% aqueous polymer solution of polyvinyl alcohol (PVOH). The Brookfield viscosity of each solution, and mixtures thereof, was determined to demonstrate the effect of rheology modification by the composition of the invention. Under visual inspection, the solutions appeared to be homogeneous. The results are presented in Table 2 below.

TABLE 2

| Test Solution | Brookfield | Viscosity (cps) | Percent Scale |
|---|---|---|---|
| 5% VP/DMAPMA/PETE/Sulfuric Acid in Water (A) | LV, 62, 10 RPM | 1470 | 48.9 |
| 5% PVOH in water (B) | LV, 00, 30 RPM | 5.2 | 26.0 |
| 50/50 (w/w) mixture of A and B | LV, 62, 20 RPM | 464 | 27.6 |

EXAMPLE 20

A 5% aqueous polymer solution of VP/DMAPMA/PETE/sulfuric acid (Ex. 1) was thoroughly mixed with a 5% aqueous polymer solution of poly-2-ethyl-2-oxazoline (PEO). The Brookfield viscosity of each solution, and mixtures thereof, was performed to demonstrate the effect of rheology modification. Under visual inspection, the solution appeared to be homogeneous. The results are presented in Table 3 below.

TABLE 3

| Test Solution | Brookfield | Viscosity (cps) | Percent Scale |
|---|---|---|---|
| 5% VP/DMAPMA/ PETE/Sulfuric Acid in Water | LV, 62, 10 RPM | 1470 | 48.9 |
| 5% PEO in water | LV, 00, 30 RPM | 4.0 | 21.3 |
| 50/50 (w/w) mixture | LV, 62, 20 RPM | 339 | 22.6 |

EXAMPLE 21

A 1% aqueous polymer solution of VP/DMAPMA/PETE/sulfuric acid (Ex. 1) was thoroughly mixed with a 1% aqueous polymer solution of Kelcoloid HVF Algin (HVF), an alginate. The Brookfield viscosity of each solution and their combination was performed to demonstrate the effect of rheology modification. Under visual inspection, the solution exhibited turbidity. The results are presented in Table 4 below.

TABLE 4

| Test Solution | Brookfield | Viscosity (cps) | Percent Scale |
|---|---|---|---|
| 1% VP/DMAPMA/ PETE/Sulfuric Acid in Water | LV, 00, 6 RPM | 60 | 58.8 |
| 1% HVF in water | LV, 62, 30 RPM | 709 | 71.4 |
| 50/50 (w/w) mixture | LV, 61, 30 RPM | 20 | 10.4 |

EXAMPLE 22

A 1% aqueous polymer solution of PVP/PETE (Ex. 4) was thoroughly mixed with a 1% aqueous polymer solution of Kelcoloid HVF Algin (HVF). The Brookfield viscosity of each solution and their combination was performed to demonstrate the effect of rheology modification. Under visual inspection, the solution appeared to be homogeneous. The results are presented in Table 5 below.

TABLE 5

| Test Solution | Brookfield | Viscosity (cps) | Percent Scale |
|---|---|---|---|
| 1% PVP/PETE in Water | LV, 00, 12 RPM | 12.4 | 24.8 |
| 1% HVF in water | LV, 62, 30 RPM | 709 | 71.4 |
| 50/50 (w/w) mixture | LV, 61, 12 RPM | 129.5 | 26.1 |

The weight fraction, $\Phi$, of particles in the composition of the invention is determined by the following procedure.
 (1) The two-phase aqueous polymeric composition is prepared as in the examples above.
 (2) The known amount of the composition is passed through a resin bed to remove insoluble particles.
 (3) A water soluble solution remains.
 (4) The solution is subjected to light to determine its differential Refractive Index.
 (5) The amount of soluble polymer which passed through the resin bed is determined.
 (6) $\Phi=1;(\#5/\#2)$.

Figure 2:
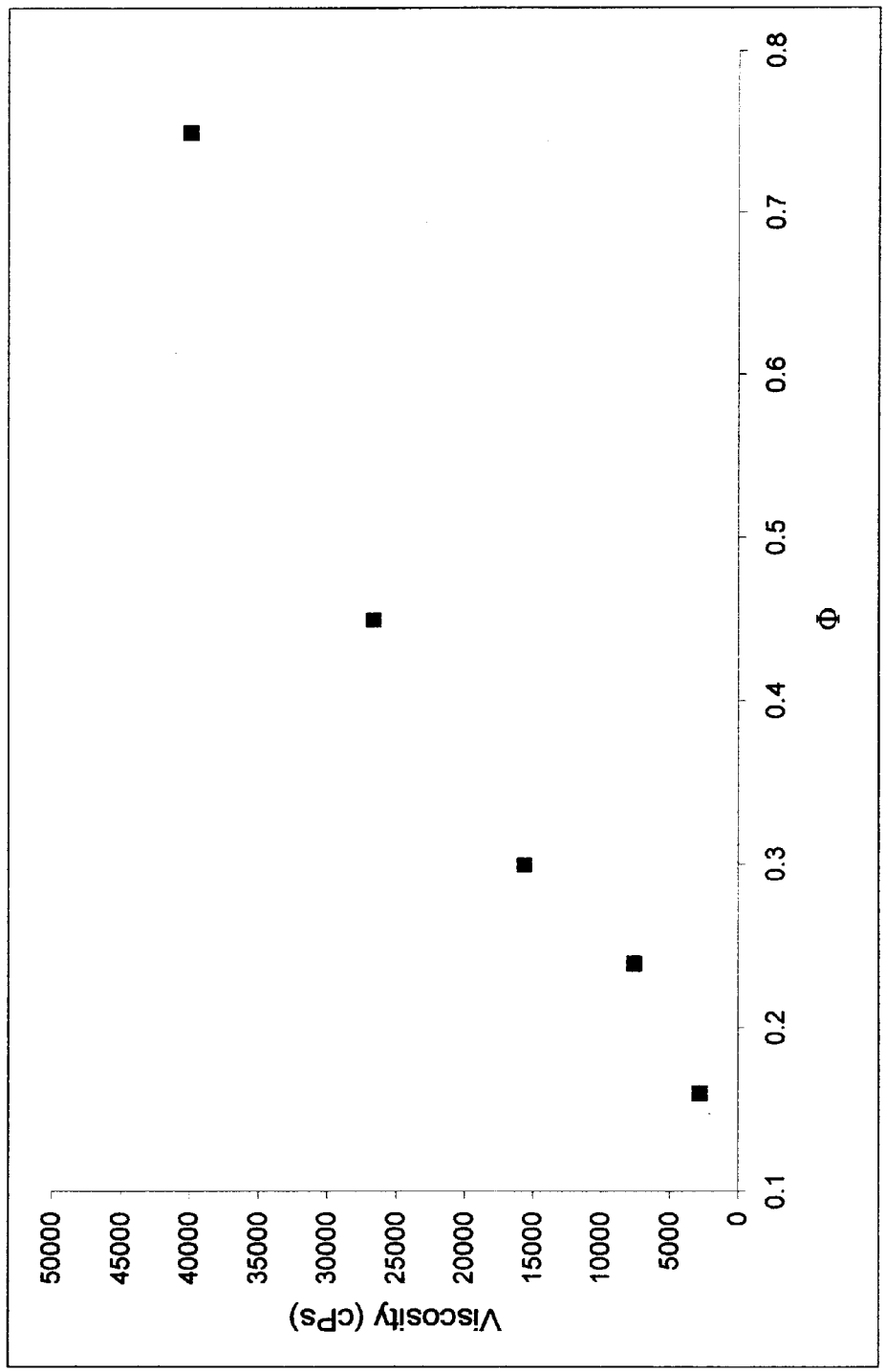
FIG. 2 is a graphical representation of Brookfield viscosity of the invention composition vs. $\Phi$ the volume fraction of particles in the composition.

FIG. 2 shows a plot of Brookfield viscosity vs. $\Phi$, the weight fraction of particles in the 2-phase polymeric composition of the invention. The graph shows a dramatic increase in viscosity of the solution with an increase in the weight fraction of the particles therein, indicating it is an effective rheology modifier.

The compositions of the invention may be admixed, if desired, with one or more of the following commercially available rheology modifiers:

Acrylic polymers, crosslinked acrylic polymers, alginates, associative thickeners, carrageenan, microcrystalline cellulose, carboxymethylcellulose sodium, hydroxyethylcellulose, hydroxypropylcellulose, hydroxypropylmethylcellulose, methylcellulose, guar and guar derivatives, locust bea gum, organoclays, polyethylene, polyethylene oxide, polyvinylpyrrolidone, silica, water-swellable clay, xanthan gum and pigments (inorganic).

Product applications of the rheology modifier of the invention include the following:

Coatings, cementitious compounds, contrast mediums, wrinkle masking, cryoprotectants, detergents, marking Instruments, flocculation moderators, personal care formulations such as skin/hair care, including shampoo, conditioner, gels and creams, pharmaceutical, such as bioadhesives, syrups and excipients), lubricating oil additives, lubricants, adhesives and cosmetics.

While the invention has been described with particular reference to certain embodiments thereof, it will be understood that changes and modifications may be made which are within the skill of the art. Accordingly, it is intended to be bound only by the following claims, in which:

What is claimed is:

1. A rheology-modified composition including an aqueous or alcoholic polymeric composition which forms a clear to translucent film upon application to a substrate comprising, by weight, 5–75% of (a) a water-soluble polymer having (b) in situ-formed, substantially water-insoluble resinous particles of said polymer substantially uniformly dispersed therein, wherein said substantially water-insoluble resinous particles are a crosslinked or branched polymer, and (c) 25–95% of water.

2. A composition according to claim 1 wherein said polymer is polyvinylpyrrolidone (PVP).

3. A composition according to claim 1 wherein said polymer is poly(vinylcaprolactam) (PVCL).

4. A composition according to claim 1 wherein said polymer is a copolymer of PVP or PVCL, and, optionally, one or more comonomers.

5. A composition according to claim 4 wherein said comonomer is dimethylaminopropyl(meth)acrylamide (DMAPMA) and dimethylaminoethyl(meth)acrylate (DMAEMA).

6. A composition according to claim 1 wherein said polymer is a copolymer of PVP and PVCL, and, optionally, one or more comonomers.

7. A composition according to claim 1 wherein said particles are <500μ.

8. A composition according to claim 7 wherein said particles are <100μ.

9. A composition according to claim 7 wherein said particles are >1 nm and <500μ.

10. A composition according to claim 1 wherein said polymer is neutralized and/or functionally neutralized and/or quaternized, and/or functionalized quaternized.

11. A composition according to claim 1 wherein the ratio of (a):(b) is 20–95% to 5–80%.

12. A composition according to claim 11 wherein said ratio is 20–75% to 25–80%.

13. A composition according to claim 1 wherein said crosslinking agent is a substantially water-insoluble compound.

14. A composition according to claim 13 wherein said crosslinking agent is pentaerythritol triallyl ether (PETE), or pentaerythritol tetraacrylate (PETA).

15. A composition according to claim 10 wherein said functional neutralization acid is a UV active based upon derivatives of cinnamic and/or benzoic and/or sulfonic and/or acetic and/or terephthalic and/or maleic acids.

16. A composition according to claim 10 wherein said functional neutralization acid is a pharmaceutically active acid.

17. A composition according to claim 10 wherein said functional neutralization acid contains silicone.

18. A composition according to claim 14 wherein said crosslinking agent is present in an amount of 0.02–0.5% by weight of said composition.

19. A composition of claim 18 wherein said amount is 0.05–0.3%.

20. A composition of claim 1 having a Brookfield viscosity of 1,000 to 45,000 cps.

21. A composition of claim 20 wherein said viscosity is 2,000 to 20,000.

22. A composition of claim 1 wherein said polymer is a vinyl lactam polymer, optionally copolymerized with a methacrylate/acrylate and/or methacrylamide/acrylamide comonomer.

* * * * *